Figure 1:
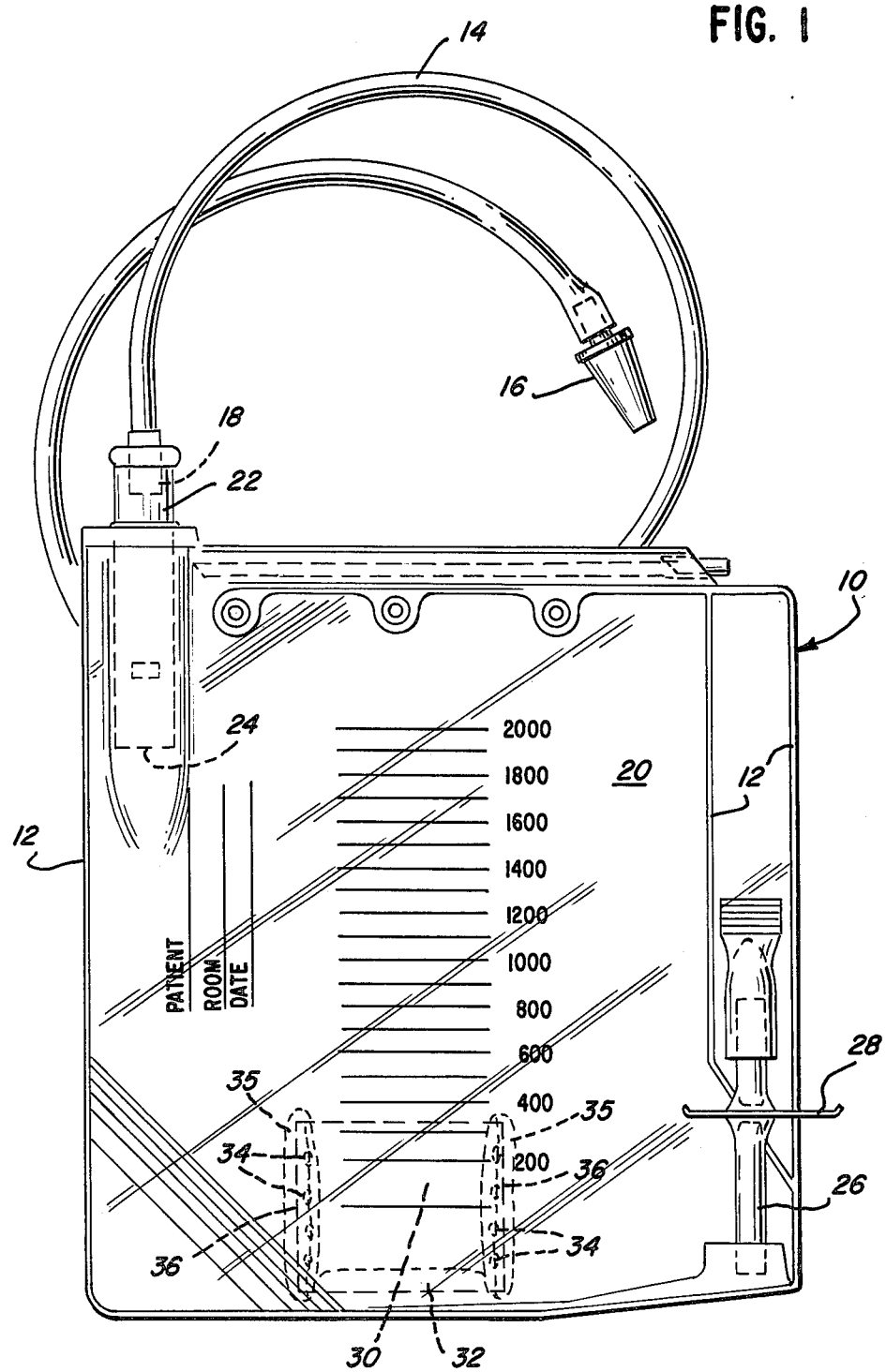

United States Patent [19]

Carpenter

[11] 4,306,029
[45] Dec. 15, 1981

[54] URINE STORAGE CONTAINERS WITH UREASE

[75] Inventor: David F. Carpenter, Buffalo Grove, Ill.

[73] Assignee: Baxter Travenol Laboratories, Inc., Deerfield, Ill.

[21] Appl. No.: 145,170

[22] Filed: Apr. 30, 1980

[51] Int. Cl.³ ............................................. C07G 15/00
[52] U.S. Cl. ................................. 435/268; 435/288
[58] Field of Search ................. 435/268, 288, 12, 317, 435/243

[56] References Cited

U.S. PATENT DOCUMENTS 3,635,798  1/1972  Kirkham et al. .................. 435/34 X
3,865,726  2/1975  Chibata et al. ....................... 210/202

Primary Examiner—Robert J. Warden
Attorney, Agent, or Firm—Paul C. Flattery; John P. Kirby; Max D. Hensley

[57] ABSTRACT

Growth and proliferation of bacteria may be inhibited in urine stored in a urine drainage container by placing urease in the container to generate sufficient ammonia to elevate the pH thereof to an alkaline level unfavorable for supporting microbial growth. Preferably, the urease is sealed in envelope means of semipermeable membrane which is capable of allowing diffusion of urea from urine stored in the container, while preventing substantial diffusion of the urease outwardly from the envelope means. Accordingly, the urease remains indefinitely reusable over many fillings and drainings of the container.

19 Claims, 1 Drawing Figure

URINE STORAGE CONTAINERS WITH UREASE

BACKGROUND OF THE INVENTION

Urinary drainage bags are medically used in large numbers for patients carrying a urinary drainage catheter. Such a urinary drainage bag usually has auxiliary means for draining without separating it from the catheter, so that the bag can be emptied and refilled over many hours or several days, without changing the bag.

As the result of this, a risk exists in the use of drainage bags that pathogenic bacteria may be accidentally innoculated into the stored urine, where they multiply. Even though most urinary drainage bags carry a drip chamber to form an air barrier and a dry wall gap, to prevent bacteria from migrating upstream from the container to the catheter, the possibility remains of the patient acquiring an infection, if the urine in the bag becomes highly infected with bacteria.

The growth and proliferation of bacteria within urine, which is an adequate growth medium, is thought to be a contributing factor to greater than one-half of all hospital-acquired urinary tract infections. The infecting bacteria may be accidentally introduced during drainage of the collected urine from the bag, unless aseptic techniques are carefully used, which of course is inconvenient, and in fact is not generally in use in hospitals.

Once the interior of the urine drainage bag is innoculated with pathogenic bacteria, growth and multiplication of the bacteria can proceed rapidly to concentrations which can be infective for the urinary tract. This is generally regarded to be 10,000 or more organisms per ml. of urine.

In accordance with this invention, urine drainage containers are modified to suppress the growth of bacteria in urine by a highly inexpensive, substantially nontoxic technique without the need for antiseptics or the like.

DESCRIPTION OF THE INVENTION

In this invention, the growth and proliferation of bacteria in urine stored in a medical urine drainage container can be inhibited by placing the enzyme urease into the container, and allowing the urine to stand in the container for at least one hour. The result of this is that ammonia can be generated from urea in the urine stored in the container. Thus it is possible to elevate the pH thereof to an alkaline level unfavorable for supporting microbial growth.

The various enzymes categorized as "urease", as is well known, hydrolyze urea in the presence of water to form carbon dioxide and ammonia, which goes into solution as ammonium hydroxide, thus elevating the pH in the alkaline direction. Most bacteria exhibit optimal growth characteristics between pH 6.5 and 7.5, which covers the pH range of normal urine. Above pH 8, bacteria growth is sharply reduced, and comes to a substantial halt at a pH of approximately 9.

The action of urease is optimal at about pH 7, with the reaction continuing until the pH of the solution in which the urease is present has risen to approximately pH 9–9.2. At this point, the action of urease tends to be inhibited.

As the result of this, a urinary drainage container which contains an adequate amount or urease, upon the addition of urine, will immediately begin to generate ammonia until the pH of the urine will have risen to the vicinity of pH 9. At this point, the action of urease ceases. However, upon the addition of fresh urine, causing the pH to drop, the urease is reactivated until the pH has risen once again to about 9, at which point the reaction is halted again.

As a result of this, the urinary drainage container becomes essentially non-infective, maintaining a pH which is not significantly toxic or caustic so that the urine can be drained from the bag in the same manner as always, yet with a strongly diminished concern about the danger of infection of the patient or the nurse through the multiplication of bacteria in the urinary drainage container.

After the urine has been drained from the container, and another amount of fresh urine comes in, the urease present in the container will act on this urine in the manner similar to its action on the previous urine, so that the urine drainage container can be emptied and refilled indefinitely.

Preferably, the amount of urease present in the container is sufficient to elevate the pH of 200 ml. of fresh urine stored at 23° C. in the container to above pH 8.0 in one hour. While this may only involve microgram quantities of purified urease, the actual material utilized may be any raw and nontoxic form of urease, for example jack bean powder, a commercially available material, for example from Worthington Biochemicals of Freehold, N.J. Other types of urease which may be utilized include urease from various known microorganisms, including molds, fungi, and bacteria.

Preferably, the urinary drainage container of this invention contains from about 7 to 20 Sumner units of urease activity and typically 8 to 10 units. As is well known, a Sumner unit of urease activity is that amount of urease capable of generating one milligram of ammonia nitrogen from a solution of 7.5 mg. of urea per 1 ml. of 0.01 M aqueous phosphate buffer at pH 7 and at 20° C. in five minutes.

Preferably, the urease, usually in a raw, dilute form, is sealed with envelope means of semipermeable membrane which is capable of allowing diffusion of urea and water from urine stored in the container into the envelope, while preventing substantial diffusion of urease outwardly from said envelope, and permitting outward diffusion of ammonia and carbon dioxide. Accordingly, stored urine is brought into contact with the envelope, causing urea and water to diffuse inwardly of the envelope to contact with the urease. There, the reaction takes place generating ammonia and carbon dioxide, which diffuses outwardly through the envelope into the urine, causing the rise in pH described above.

When the urine is drained from the container, it is preferred for the envelope means to be of such a character that the urease does not pass out of the drain, being retained by the envelope in the container, but remains for interaction with the next aliquot of urine to be added to the container.

A large variety of semipermeable membrane techniques for enclosing enzymes in semipermeable envelopes are known. For example, in Chibata et al. U.S. Pat. No. 3,865,726, microcapsules containing urease are disclosed. Such microcapsules could be retained in a liquid-permeable fabric container and utilized in accordance with this invention.

It is intended that the term "envelope means" is intended to include microcapsules of semipermeable membrane material, as well as larger, semipermeable-membrane, sealed envelope structures. Specifically, an acrylamide monomer in the solution containing urease may be microencapsulated in accordance with known technology. Nylon, polyurea or the like may also be utilized, as taught in the patent cited above, and in accordanced generally with the considerable body of available technology in that area.

Alternatively, the envelope means of this invention may be made from semipermeable membrane sheeting, for example cellulose-type materials, polycarbonate resins, polyvinyl alcohol, or any other known semipermeable material capable of providing mass transfer to urea, ammonia, water, and carbon dioxide as described above.

By way of specific example, a length of tubing made out of cuproammonium cellulose sheeting, a well known material used in membrane dialyzers, may be utilized in accordance with this invention. A short length of the flattened tubing may receive the urease, which may only comprise a small fraction of a gram of a raw urease material such as jack bean powder, and then both ends of the cuproammonium cellulose tubing may be sealed by means of a hot-melt potting or sealing compound such as polyvinylchloride thermoplastic sealant. Holes may be punched through the flattened cellulose tubing for containing the urease material adjacent the ends, so that the hot melt or other sealing compound may pass through the holes and surround the ends of the flattened tubing, with the sealing compound forming a unitary sealing mass at each end of the tubing.

The resulting envelope, containing urease, is then preferably placed in dry form in a urine drainage container, specifically a standard urinary drainage bag of any design, with the urinary drainage bag being then sealed. The urinary drainage bag may then be sterilized, preferably by an ethylene oxide or a beta or gamma radiation technique, which may cause a reduction of about ten percent of the enzyme activity of the urease present in the bag. This can be accounted for by the amount of raw urease initially placed in the envelope. Following this, the urinary drainage bag may be stored until used.

Referring to the drawing, FIG. 1 is an elevational view of a urinary drainage bag utilizing the invention of this application.

Referring to FIG. 1, urinary drainage bag 10 is of generally-known design except as otherwise described herein, being made of polyvinyl chloride sheeting and sealed along heat seal lines 12. Bag 10 defines a flexible drainage tube 14 having a drainage catheter adapter 16 attached to one end thereof, and being attached at its other end 18 to urine storage container 20.

An air barrier drip chamber 22 is provided, so that the end 18 of drainage tube is separated from the walls of drip chamber 22, the bottom end 24 of drip chamber 22 being open to permit the free flow of urine into storage container 20 without wetting the walls of drip chamber 22. Accordingly, a dry barrier is formed, tending to prevent the upward migration of bacteria from storage container 20 through drainage tube 14 to the bladder of the patient.

Nevertheless, when a substantial amount of heavily-infected urine occupies storage container 20, it has been found that infections can result.

Bottom drain member 26 is provided, having a known fold-up feature as shown and a slide clamp 28 for intermittent drainage of urine from storage container 20.

In accordance with this invention, envelope means 30 is placed within urine storage container 20. Envelope 30 contains an effective amount, as described above, of urease 32, for example, in the dilute form of jack bean powder or a urease-containing extract thereof.

Envelope member 30 may specifically comprise a two or three inch length of flattened cuproammonium cellulose tubing, specifically Cuprophan of a grade and quality suitable for use as hemodialysis membrane having a wall thickness, for example, on the order of 10 or 20 microns. Such membrane is commercially available.

At each end of the short length of cuproammonium cellulose tubing 30, a plurality of holes 34 are formed through both layers of the flattened tubing adjacent the ends thereof. A hot melt potting compound, for example thermoplastic materials such as nylon or poly(ethylene-vinyl acetate), may be applied to the ends of envelope 30, flowing through the holes 34 and surrounding each end 36 of envelope 30, being locked to the ends of the envelope 30 since the hot melt compound 35 flows prior to hardening through hole 34, and forms a unitary mass about each of the ends 36 of envelope 30 to seal the urease material 32 within envelope 30. One end of envelope 30 may be sealed in this manner. Then the urease may be placed in the envelope, and the other envelope end may be similarly sealed.

Envelope 30 is then placed in container 20, which is then conventionally sealed, sterilized, and stored under dry conditions.

Since the semipermeable walls of envelope 30 are readily permeable to urea and water of the urine, such materials diffuse into the interior of the envelope 30 when drainage bag 10 is put into operation for storing urine. A quick reaction takes place forming ammonia and carbon dioxide, which are capable of diffusing outwardly through the walls of envelope 30 into the urine in the bag, with the result that over a period of about an hour the pH of the urine in the bag can climb beyond 8 up toward pH 9 or 9.2, at which point the reaction ceases. Because of this, growth of bacteria is heavily inhibited while the urine is stored in bag 10.

The above has been offered for illustrative purposes only, and is not intended to limit the invention of this application, which is as defined in the claims below.

That which is claimed is:

1. The method of inhibiting the growth and proliferation of bacteria of urine stored in a urine drainage container, which comprises placing urease in said container and allowing said urine to stand in the container until sufficient ammonia is generated from urea in said urine stored in the container to elevate the pH thereof to an alkaline level unfavorable for supporting microbial growth.

2. The method of claim 1 in which said urease is in the form of a material selected from the group consisting of jack bean powder and urease-containing extracts thereof.

3. The method of inhibiting the growth and proliferation of bacteria of urine stored in a medical urine drainage container, which comprises placing urease in said container, said urease being sealed in said container within an envelope made of semipermeable membrane capable of allowing passage of urea, water, ammonia, and carbon dioxide but incapable of allowing the passage of substantial amounts of urease across said membrane, until sufficient ammonia is generated from urea of urine stored in said container to elevate the pH thereof to an alkaline level unfavorable for supporting microbial growth.

4. The method of claim 3 in which said urease is in the form of jack bean powder.

5. The method of claim 3 in which said container includes from 7 to 20 Sumner units of urease.

6. The method of claim 3 in which sufficient urease is present in said container to raise the pH of 200 ml. of fresh urine to above 8.0 at 23° C. in one hour.

7. A urine storage container which includes therein an envelope coantaining urease, said envelope comprising semi-permeable membrane capable of allowing passage of urea, water, ammonia and carbon dioxide, but incapable of allowing the passage of substantial amounts of urease across said semipermeable membrane.

8. A urine drainage container comprising a flexible drainage tube, a urinary drainage catheter adaptor attached to one end thereof, and a urine storage container attached to the other end thereof, the improvement comprising, a quantity of urease positioned within said storage container sufficient to elevate the pH of 200 ml of urine stored at 23° C. in said container to above pH 8.0 in one hour.

9. The container of claim 8 in which said storage container is a flexible, plastic bag defining means for intermittently draining said urine by a route other than said flexible drainage tube.

10. The container of claim 8 in which said urease is in the form of jack bean powder.

11. The container of claim 8 in which 7 to 20 Sumner units of urease are present in said storage container.

12. A urine drainage container having access means for placing urine therein and removing urine therefrom, said drainage container carrying in its interior a quantity of urease sealed in envelope means comprising semipermeable membrane which is capable of allowing inward diffusion of urea and water from urine stored in said container and outward diffusion of ammonia and carbon dioxide, while preventing substantial diffusion of said urease outwardly from said envelope, whereby stored urine may be drained from said container without loss of said urease.

13. The urine drainage container of claim 12 which is a flexible plastic envelope defining means for intermittently draining said urine by a route other than through said access means.

14. The urine drainage container of claim 12 in which sufficient urease is present to elevate the pH of 200 ml of fresh urine stored at 23° C. in said container to above 8.0 in one hour.

15. The container of claim 12 in which from 7 to 20 Sumner units of urease are present in said drainage container.

16. The urine drainage container of claim 12 in which said semipermeable membrane is a cellulose-based membrane.

17. The urine drainage container of claim 16 in which said semipermeable membrane is made of cupraammonium cellulose.

18. The urine drainage container of claim 12 in which said urease is in the form of jack bean powder.

19. A urine drainage container having access means for placing urine therein, said drainage container carrying in its interior a sufficient quantity of materials selected from a group consisting of jack bean powder and urease-containing extracts of jack bean powder to cause 200 ml of fresh urine stored at 23° C. in said container to achieve a pH of above 8.0 in one hour.

* * * * *